United States Patent
Ten Kate

(10) Patent No.: US 10,147,298 B2
(45) Date of Patent: Dec. 4, 2018

(54) SYSTEM AND METHOD FOR MONITORING ACTIVITIES OF DAILY LIVING OF A PERSON

(71) Applicant: KONINKLIJKE PHILIPS N.V., Eindhoven (NL)

(72) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/542,257

(22) PCT Filed: Jan. 7, 2016

(86) PCT No.: PCT/EP2016/050144
§ 371 (c)(1),
(2) Date: Jul. 7, 2017

(87) PCT Pub. No.: WO2016/113162
PCT Pub. Date: Jul. 21, 2016

(65) Prior Publication Data
US 2017/0365149 A1 Dec. 21, 2017

(30) Foreign Application Priority Data
Jan. 12, 2015 (EP) .................................. 15150861

(51) Int. Cl.
| | | |
|---|---|---|
| *G08B 21/04* | (2006.01) | |
| *G16H 40/67* | (2018.01) | |
| *A61B 5/00* | (2006.01) | |
| *A61B 5/11* | (2006.01) | |
| *G08B 29/18* | (2006.01) | |

(Continued)

(52) U.S. Cl.
CPC ........ *G08B 21/0453* (2013.01); *A61B 5/0002* (2013.01); *A61B 5/0022* (2013.01); *A61B 5/1118* (2013.01); *A61B 5/1123* (2013.01); *A61B 5/7282* (2013.01); *A61B 5/746* (2013.01); *G06F 19/00* (2013.01); *G06N 5/04* (2013.01); *G08B 21/0423* (2013.01); *G08B 21/0492* (2013.01); *G08B 29/185* (2013.01); *G08B 29/188* (2013.01); *G16H 40/67* (2018.01); *A61B 2503/08* (2013.01); *A61B 2505/07* (2013.01); *A61B 2560/0252* (2013.01)

(58) Field of Classification Search
CPC ............ G08B 21/0453; G08B 21/0423; A61B 5/0002; A61B 5/11183; A61B 5/1123; A61B 5/7282; A61B 5/746; G06N 5/04
USPC ....................................................... 340/573.1
See application file for complete search history.

(56) References Cited

U.S. PATENT DOCUMENTS

| | | |
|---|---|---|
| 7,095,328 B1 | 8/2006 | Stern et al. |
| 2008/0001735 A1 | 1/2008 | Tran |

(Continued)

*Primary Examiner* — Jack K Wang

(57) ABSTRACT

Presented is a system and method for monitoring activities of daily living, ADLs, of a person within an environment. The system comprises an ADL inference unit adapted to receive a sensor output signal representative of a detected value of a property of at least one of: the person; and the environment, and to generate an inferred ADL output signal representative of the inferred ADL of the person. A monitor unit is adapted to generate a monitor signal dependent on at least one of: the received sensor output signal; and the inferred ADL output signal.

13 Claims, 7 Drawing Sheets

(51) Int. Cl.
*G06N 5/04* (2006.01)
*G06F 19/00* (2018.01)

(56) References Cited

U.S. PATENT DOCUMENTS

| | | | | |
|---|---|---|---|---|
| 2009/0184821 | A1* | 7/2009 | Kuris | G08B 21/0461 340/541 |
| 2014/0129160 | A1* | 5/2014 | Tran | H02J 3/14 702/61 |
| 2015/0070172 | A1* | 3/2015 | Alasaarela | A61B 5/0022 340/573.1 |
| 2015/0100245 | A1* | 4/2015 | Huang | A61B 5/0022 702/19 |
| 2015/0302310 | A1* | 10/2015 | Wernevi | G16H 50/20 706/12 |
| 2016/0107031 | A1* | 4/2016 | Palatsi | A63B 24/0075 434/247 |
| 2017/0261951 | A1* | 9/2017 | Bandara | G06Q 10/06312 |

* cited by examiner

SYSTEM AND METHOD FOR MONITORING ACTIVITIES OF DAILY LIVING OF A PERSON

CROSS-REFERENCE TO PRIOR APPLICATIONS

This application is the U.S. National Phase application under 35 U.S.C. § 371 of International Application No. PCT/EP2016/050144, filed on Jan. 7, 2016 which claims the benefit of European Patent Application No. 15150861.1, filed on Jan. 12, 2015. These applications are hereby incorporated by reference in their entirety herein.

FIELD OF THE INVENTION

This invention relates to a system and method for monitoring activities of daily living of a person.

BACKGROUND OF THE INVENTION

Functional assessment or monitoring of a person's health status, physical abilities, mental abilities, or recuperation after injury, hospitalization and treatment is of primary concern in most branches of medicine, including geriatrics, rehabilitation and physical therapy, neurology and orthopedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they living independently in their own home or within familiar surroundings. For example, one such known system for detecting activities of daily living of a person comprises three main components: (i) a sensor system that collects information about the person's activities and behaviours; (ii) an intelligence (or information processing) system that interprets the sensor signals for the care needed; and (iii) a user interface system that enables care givers to inspect the interpreted (processed) information. The intelligence system typically makes use of computational techniques known in the art as artificial intelligence. The system may be supported by conventional technologies for data collection, transmission, and storage.

In practice, however, a major difficulty is encountered by the wide range of variations that can happen in actual care cases. For example, people can live in differently architected houses, have different lifestyles and habits. Care givers may also have different needs, locations and/or lifestyles. Also, different people may have different care needs and so differing aspects of the activities and behaviours may be of interest for monitoring. Since there are so many possible circumstances, situations and contexts that can occur in daily life, it is difficult to capture all of them in a single knowledge base as well as to detect them all from a range of sensor signals. Thus, there are very likely to be exceptions that are not covered by the conventional system(s).

Also, the ever-increasing complexity in striving to cover all possible contexts and situations requires more expensive systems, and also leads to increased (i.e. slower) response times.

Accuracy, or the amount of relevant information generated, may also be reduced by trying to cater for a large number of alternate situations. For example, although many situations may not be relevant to a monitored person, these irrelevant situations may still be accounted for and selected by the system, thus providing erroneous responses.

SUMMARY OF THE INVENTION

The invention is defined by the claims.

According to a first aspect of the invention, there is provided a system for monitoring activities of daily living, ADLs, of a person within an environment, the system comprising: an ADL inference unit adapted to receive a sensor output signal representative of a detected value of a property of at least one of: the person; and the environment, and to generate an inferred ADL output signal representative of an inferred ADL of the person; and a monitor unit adapted to generate a monitor signal dependent on at least one of: the received sensor output signal; and the inferred ADL output signal.

The invention is based on the insight that a system for monitoring ADLs of a person can be used to generate a monitor signal for an alerting or warning system which can indicate the person is in need of help, for example. It is proposed to generate such a monitor signal from either of two types of information, or from a combination of both types of information. The first type of information may relate to an ADL of the person that is inferred from a sensor output signal, and the second type of information may relate to the (raw or sampled) sensor output signal itself. In other words, a monitor signal may be generated based on an inferred ADL, wherein the ADL has been inferred (by an inference system) from one or more sensor signals, or a monitor signal may be generated based directly on one or more sensor signals (i.e. by-passing the inference system and the inferred ADLs.).

Thus, inferred ADLs may be provided as an input to a first part of a monitor unit, and the first part of the monitor unit may generate an alert signal dependent on the inferred ADLs. In this way, the first part of the monitor unit may use the inferred ADLs to enable the creation of simple warnings & alerts. However, in addition, a second part of the monitor unit may be provided with sensor data/signals directly (i.e. by-passing the ADL inference unit) and the second part of the monitor unit may generate an alert signal dependent on the sensor data/signals directly. The second part of the monitor unit may therefore use raw sensor data/signals to enable the creation of highly specific and/or accurate warnings and alerts.

Furthermore, the monitor unit may combine the raw sensor data/signals with the inferred ADLs, thus providing a hybrid form of alert.

There exist many sensors that can be employed by embodiments. Typical sensors include PIR (Passive Infra Red; measure movement and presence), OC (open-close; measure state of doors, in particular front doors, windows, and cupboards, including refrigerators), power sensors (measure current consumption of appliances, such as microwave, water cookers, TV, etc), and pressure mats (measure occupancy of user sitting in chair, lying in bed, standing on door mat in front of front door, etc). Many others exist and are conceivable, such as sensors to signal light switch state, or sensors that measure environmental conditions such as humidity, $CO_2$ level (or CO and smoke), etc. A further range of sensors are those based on physical quantities, such as accelerometers, magnetometers, gyroscopes, and air pressure sensors. Accelerometers, for example, can also measure state of doors and their open-close movements. Yet another range of sensors consists of microphones and cameras (including infra-red (IR), or even UV and beyond, part of spectrum), to which also belong GPS and location-sensitive IR. Ultra-sound or RF-based sensors, including RFID tagging, provide additional input. Appliances having an own IP-address, known as the Internet-of-things, provide further sensor input signals that can be taken by the smart-home system.

Although the sensor(s) may be mounted in the environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof.

The sensors may also be adapted to undertake primary processing of the detected values, such a signal filtering, sampling, conditioning, etc., so as to reduce a required transmission bandwidth and/or transmission duration for example.

Non-intrusive monitoring may therefore be realized with relative simple sensors that provide data on specific ambient conditions or properties/parameters of the environment (such as temperature or humidity for example), or properties of the person (such as movement, for example). Such sensors for measuring ambient condition or properties/parameters of the environment may be simple, small and/or cheap. Also, the movement of the person may be detected with, for example, a Passive InfraRed (PIR) sensor which is a cheap component. Movement sensors may be used to switch on lighting and people are therefore typically familiar with their usage. Thus, embodiment may employ sensors that are considered to be non-intrusive and more easily accepted by the monitored person. Yet, with the data provided by these sensors, ADLs may be determined and provide more information on the person being monitored.

For example, with a humidity sensor and a movement sensor in the bathroom it may be inferred that the person is taking a shower. In a further example, with a temperature sensor and a movement sensor in the kitchen it may be determined that the person is preparing a hot meal. It is a further advantage that the sensors may be stationary sensors that are located for example in the bathroom and in the kitchen, thus making it unnecessary for the person to wear a device.

Activities of daily living concern basic activities that a person executes on a regular basis. Examples of activities of daily living are eating; cooking; medicating; sleeping; toileting; bathing; washing, etc. Embodiments may thus provide information on the ADLs of a person in a non-intrusive manner.

In an embodiment, the ADL inference unit may comprise: a first inference subsystem adapted to receive the sensor output signal, to infer a primitive ADL event based on the received sensor output signal, and to generate a primitive ADL signal representative of the inferred primitive ADL event; and a second inference subsystem adapted to receive the primitive ADL signal, to infer an aggregate ADL event from the received primitive ADL signal, and to generate an aggregate ADL signal representative of the inferred aggregate ADL event. The ADL inference unit may then be adapted to generate the inferred ADL output signal dependent on at least one of: the primitive ADL signal; and the aggregate ADL signal. The ADL inference unit may thus be adapted to generate the inferred ADL output signal based on the primitive ADL signal from the first inference subsystem and the aggregate ADL signal from the second inference subsystem. The inferred ADL output signal may therefore depend on an inferred primitive ADL event and an inferred aggregate ADL event. Inferred primitive and aggregate ADL events may therefore be used to generate an ADL output signal that is representative of an inferred ADL of the person.

Thus, there may be proposed a concept of casting the inference of ADLs in a rule-based formalism (e.g. a rule-based inference method). The expression "rule-based" is to preferably be understood in a wide sense so that it not only refers to systems that use a rule language, but also (logic) systems that are equivalent to or resemble rules. For example, ontologies may be implemented by a rule-based system which employs language about sets and subsets, wherein a subset relation can be viewed as equivalent to a rule statement (e.g. the relationship "A is a subset of B" is equivalent to the rule "if A then B").

Further, because rule-based systems (and logic-based systems in general) can suffer from high computational complexity, only a part of the inference may be cast in the rule-based formalism so as to maintain computational complexity within acceptable bounds.

In particular, it has been realised that ADL events can be distinguished between based on whether they are "primitive" or "aggregate" events. Primitive ADL events may be inferred outside a formalised inference system/method (i.e. inferred directly from raw sensor output signals). Primitive ADL events may then serve as input to the rules that create aggregate ADL events. In other words, aggregate ADL events may be formed based on a plurality of primitive ADL events.

By way of example, a primitive event may relate to a time instant, whereas an aggregate event may relate to a time interval. Thus, a characteristic of an aggregate event may be that it covers a period of time that is at least as long as that of the primitive ADL event. By making a distinction based on the properties of primitive and aggregate events with respect to time, the design of inference algorithms, and the corresponding processing, may be simplified.

Put another way, there may be two types of inferred events: primitive and aggregate, denoted EventP and EventA, respectively. Primitive events may be time instants that indicate a transition in an ADL. Aggregate events, on the other hand, may be time intervals that hold the complete duration of the ADL.

Thus, as depicted in FIG. 1, primitive events 2 may be inferred from sensor events 1, for example by detecting time instants of an ADL beginning or ending. Aggregate events 3 may be inferred from the primitive events 2, for example from a time interval between the detected ADL 'begin' and 'end' time instants. In both inference procedures, additional state is maintained which is used upon the next cycle of inference with the next input events.

It also noted a further level of aggregate events may be identified, wherein an aggregate event is inferred from another aggregate event. Thus, it will be understood that an aggregate event may be inferred from a primitive event, another aggregate event, or from a combination of primitive and aggregate events. In other words, primitive events may be inferred from sensor events, whereas aggregate events may not be inferred directly from sensor events.

By inferring primitive ADL events directly from raw sensor output signals, and then inferring aggregate ADL events from primitive and/or aggregate ADL events using an inference method, it will be appreciated that only a sub-part of the ADL inference may be cast in a formalised inference definition. This may reduce computational complexity and may also enable a user of the system (such as the care giver or medical practitioner, for example) to create, define, modify, alter rules and constraints. Embodiments may therefore enable aggregate ADL events to be defined, modified, and extended by a user, thereby providing the flexibility to the many different contexts in which the system operates. Embodiments may also enable some of the processing load to be distributed throughout the system. For example, pre-processing may be undertaken at a sensor so that primitive event generation or inference may be implemented at the sensor(s). Alternatively, or additionally, processing could be undertaken at a communication gateway. In some embodiments, processing may be undertaken at a remote gateway or server, thus relinquishing processing requirements from an end-user or output device. To enable users to modify the rules, editing of primitive events may be hosted in the monitored environment (e.g. house), whereas editing of aggregate event may be done remotely at a central server. Such distribution of processing and/or hardware may allow for improved maintenance abilities (e.g. by centralising complex or expensive hardware in a preferred location). It may also enable computational load and/or traffic to be designed or located within a networked system according to the processing capabilities available. A preferable approach may be to process sensor data locally and transmit extracted events (for example, open close from accelerometer data) for full processing at a remote server.

Further, alerts or warnings may be generated based on the occurrence of such user-defined ADL events. It may also enable only part of the inference system/approach to employ a rule-based inference method, thus reducing processing requirements while also enabling the inference of an ADL based on primitive and aggregate ADL events.

By using a logic-based system for ADL inference, the programming complexity for a user is kept simple (by virtue of the declarative language that can be used). Also, to further ease a user's effort, additional logic and knowledge bases can be employed, such as ontologies. These may further simplify the provision of the rules by a user. Proposed embodiment may therefore require almost zero programming skills.

There is therefore proposed an ADL inference unit for inferring an ADL of a person based on the received sensor output signal, wherein the ADL inference unit comprises: a first inference subsystem adapted to receive the sensor output signal, to infer a primitive ADL event based on the received sensor output signal, and to generate a primitive ADL signal representative of the inferred primitive ADL event; and a second inference subsystem adapted to receive the primitive ADL signal, to infer an aggregate ADL event from the received primitive ADL signal using a rule-based inference method, and to generate an aggregate ADL signal representative of the inferred aggregate ADL event, and wherein ADL inference unit is adapted to generate an inferred ADL output signal dependent on at least one of: the primitive ADL signal; and the aggregate ADL signal.

The ADL inference unit may further comprise a rule input interface adapted to receive an input for defining or modifying one or more rules of the rule-based inference method.

There is also proposed a method for inferring an ADL of a person based on a sensor output signal, where in the method comprises: inferring a primitive ADL event based on the sensor output signal; generating a primitive ADL signal representative of the inferred primitive ADL event; inferring an aggregate ADL event from the primitive ADL signal using a rule-based inference method; and generating an aggregate ADL signal representative of the inferred aggregate ADL event. The step of generating an inferred ADL output signal may then be dependent on at least one of: the primitive ADL signal; and the aggregate ADL signal.

Embodiments thus propose the division of programming logic so that only part of an ADL inference system/method employs a rule-based structure, thereby reducing or relieving computational complexity. Embodiments of the proposed ADL inference unit may therefore be employed in a system for monitoring ADLs of a person within an environment.

Proposed embodiments may further comprise a rule input interface adapted to receive an input for defining or modifying one or more rules of the rule-based inference method.

In an embodiment, the system may further comprise a user input interface adapted to receive a user input for defining or modifying one or more alert conditions, and the monitor unit may then be adapted to generate the monitor signal further dependent on the one or more alert conditions.

In a further embodiment the monitor unit may be adapted to generate the monitor signal based on a comparison of the received sensor output signal with a predetermined threshold. For example, this provides the advantage that for example an alarm may be given if the person stays too long in the bathroom with the hot shower running indicating that for example the person has become unwell in the bathroom.

In a further embodiment of the system the ADL inference unit may be further adapted to store the inferred ADL of the person in an activity database. Thus, the behavioural pattern of activities of the person may be stored. Shifts in this pattern may indicate that the person is in need of help. For example, the person may start forgetting to take a regular shower. Or in a further example the person is taking less frequently a hot meal because he/she is feeling depressed.

In a further embodiment, the monitor unit may be further adapted to detect an irregularity in the activity database. For example, by adding time information to the measured property of the environment (such as an ambient condition like humidity or temperature), the time spent between the activities may be determined. With the time information, the frequency of the activity may be determined. For example, the frequency of the determined activity 'preparing a hot meal' may be 'once a day', or '5 times a week'. An irregularity in the activity database may then, for example, be that the time spent between the determined activities of 'preparing a hot meal' has increased. For example the average time spent may be determined using the data from the activity profile. When the time spent between two successive determined activities of 'preparing a hot meal' is larger than for example 1.5 times the average time spent this indicates an irregularity.

Embodiments may further comprise a sensor adapted to detect a value of a property of at least one of: the person; and the environment; and to generate the sensor output signal representative of the detected value.

In a further embodiment the monitor unit may be further arranged to generate an alert signal in response to the detected irregularity. The irregularity may indicate that the person is in need of help. In a further example, a medical practitioner, a caregiver, a family member or close relative may be advised by the system (using the alert signal) to pay a visit to the person.

In a further embodiment the monitor signal may be given to the person himself/herself. For example, the warning signal may be a feedback signal advising the person to take a certain medication.

The invention further provides a method for monitoring activities of daily living (ADLs) of a person within an environment, the method comprising: inferring an ADL of the person based on a sensor output signal representative of a detected value of a property of at least one of: the person; and the environment; generating an inferred ADL output signal representative of the inferred ADL of the person; and generating a monitor signal dependent on at least one of: the sensor output signal; and the inferred ADL output signal wherein the step of inferring an ADL comprises: inferring a primitive ADL event based on the sensor output signal; generating a primitive ADL signal representative of the inferred primitive ADL event; inferring an aggregate ADL event from the primitive ADL signal; and generating an aggregate ADL signal representative of the inferred aggregate ADL event, and wherein the step of generating an inferred ADL output signal ADL is based on the primitive ADL signal and the aggregate ADL signal.

The non-intrusive character of the monitoring is in the method realized by measuring at least one ambient condition of the person rather than by for example surveillance by camera of the person.

In a further embodiment of the method, the inferred ADL of the person may be stored in an activity database. The stored activities of the person may form a behavioural pattern that characterizes said person. Deviations in the monitored activities of the person may be used as an indicator of the well being of the person. For example elderly people that start suffering from dementia will typically exhibit shifts in their behavioural pattern. They will start to forget to take a shower and lose the feeling of time. Therefore, in a further embodiment of the method the activity database may be analyzed for irregularities or shifts in the behavioural patterns. An irregularity in the activity database may be detected, and an alert signal generated in response to the detected irregularity According to yet another aspect of the invention, there is provided a computer program product for monitoring activities of daily living, ADLs, of a person within an environment, wherein the computer program product comprises a computer-readable storage medium having computer-readable program code embodied therewith, the computer-readable program code being configured to perform all of the steps of an embodiment.

According to yet another aspect of the invention, there is provided a computer program product for inferring an ADL of a person based on a sensor output signal, wherein the computer program product comprises a computer-readable storage medium having computer-readable program code embodied therewith, the computer-readable program code being configured to perform all of the steps of an embodiment.

In an embodiment, a computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of a method of controlling an autonomous according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Figure 1:
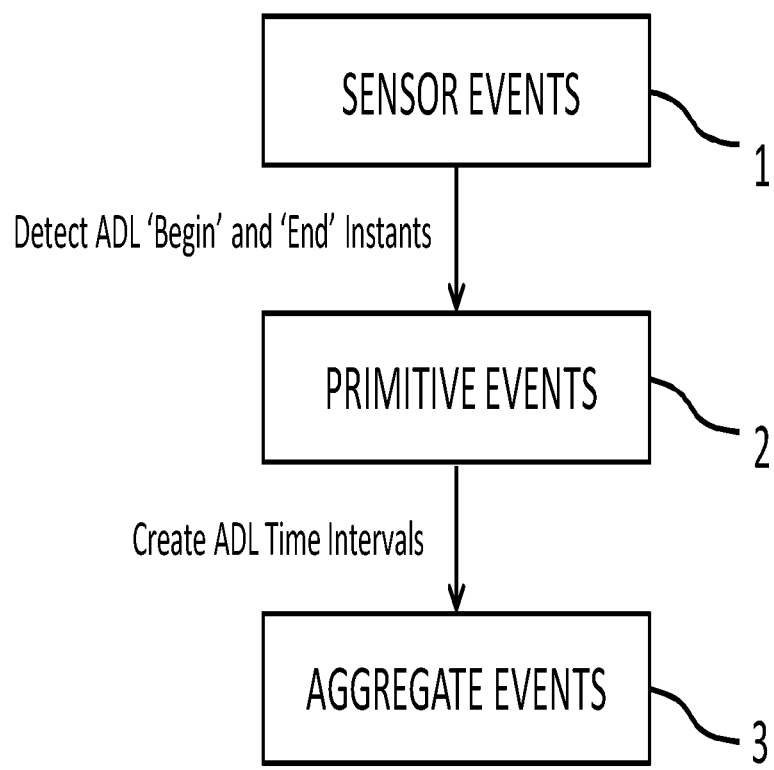
FIG. 1 is simplified block diagram depicting an exemplary relationship between sensor events, primitive events and aggregate events.

Proposed is a concept for monitoring activities of daily living, ADLs, of a person within an environment. Persons that may be monitored by embodiment may, for example, include a disabled person, an elderly person, an injured person, a medical patient, etc.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

It has been recognized that in many care situations there is a need to be informed about the ADLs a person is performing. There may also be a need to be alerted when an anomaly occurs. The type of anomaly can be different per case. A large class of anomalies relate to aberrations in an ADL routine of the person. For example, an above average number of toilet visits during the night. More severe incidents form another class, for example falls by the person.

Further refined algorithms may also be needed when a (declining) trend in activity is to be detected.

By way of example, ADLs may include:
 (i) Medication
  a. Is the elder taking his medicine in proper way at proper moments?
 (ii) Sleep
  a. Is the elder sleeping sufficiently and undisturbed?
 (iii) Eating/Drinking
  a. Is the elder eating sufficiently and regularly?
  b. Does he prepare meals by himself?
 (iv) Physical activity
  a. Is the elder active during the day?
  b. Is there little sedentary behaviour?
 (v) Toileting
  a. Is the elder toileting in normal way?
  b. Are there frequent visits to the toilet during the night?
 (vi) Bathing
  a. Is the elder bathing adequately?
 (vii) Being In/Out House
  a. Is the elder going out?
 (xiii) Ambient climate
  a. Is the environment "clean"?
  b. E.g., is temperature proper, is the $CO_2$ level healthy?
 (ix) Etc.

Based on the above exemplary ADLs, the following examples warnings and alerts may be:
 A. Sign of activity, or sign of inactivity
 B. Presence in rooms considered risky (e.g. alone in kitchen when elder is suffering dementia)
 C. Leaving the house at unexpected moments, such as during the night
 D. Exceptional frequency or exceptional duration of toilet visits
 E. Exceptional duration of bathing
 F. Sleeping shorter
 G. Reduced activity
 H. Etc.

Embodiments of the present invention are therefore directed toward enabling ADLs of a person to be detected and/or monitored. This may be used to generate an alert signal for an alerting or warning system that can indicate the person is in need of help, for example.

Embodiments are based on the insight that a system for monitoring ADLs of a person can be used to generate a monitor signal for an alerting or warning system. It is proposed to generate such a monitor signal from either two types of different information, or from a combination of both types of information. The first type of information may relate to an ADL of the person that is inferred from a sensor output signal (in other words, an inferred ADL), whereas the second type of information may relate to the sensor output signal itself. In other words, embodiments may be based on the concept that a monitor signal may be generated based on an inferred ADL or based directly on one or more sensor signals. Inferred ADLs may therefore be used a first input of an alert generating unit, and raw sensor signals/data may be used as a second input of the alert generating unit.

Also proposed is a concept of basing the inference of ADLs on a rule-based formalism. Further, only a part of the inference may use the rule-based formalism so as to reduce overall computational complexity. In particular, it has been realised that ADL events can be distinguished between based on whether they are "primitive" or "aggregate" events. Primitive ADL events may be inferred directly from raw sensor output signals (i.e. outside the rule-based inference system/method). Primitive ADL events may then serve as an input to the rules that create aggregate ADL events. Aggregate ADL events may thus be formed based on a plurality of primitive ADL events. Put another way, only a sub-part of the ADL inference may be cast in a rule-based formalism. This may enable a user of the system (such as the care giver or medical practitioner, for example) to create, define, modify, alter rules and constraints. Embodiments may therefore enable aggregate ADL events to defined, modified, and extended by a user, thereby providing the flexibility to the many different contexts in which the system operates. Also, alerts or warning may be generated based on the occurrence of such user-defined ADL events.

Embodiments thus propose the division of an ADL inference system/method so that only part of an ADL inference system/method employs a rule-based structure. Such a proposed ADL inference system/method may therefore be employed in a system for monitoring ADLs of a person within an environment.

Figure 2A:
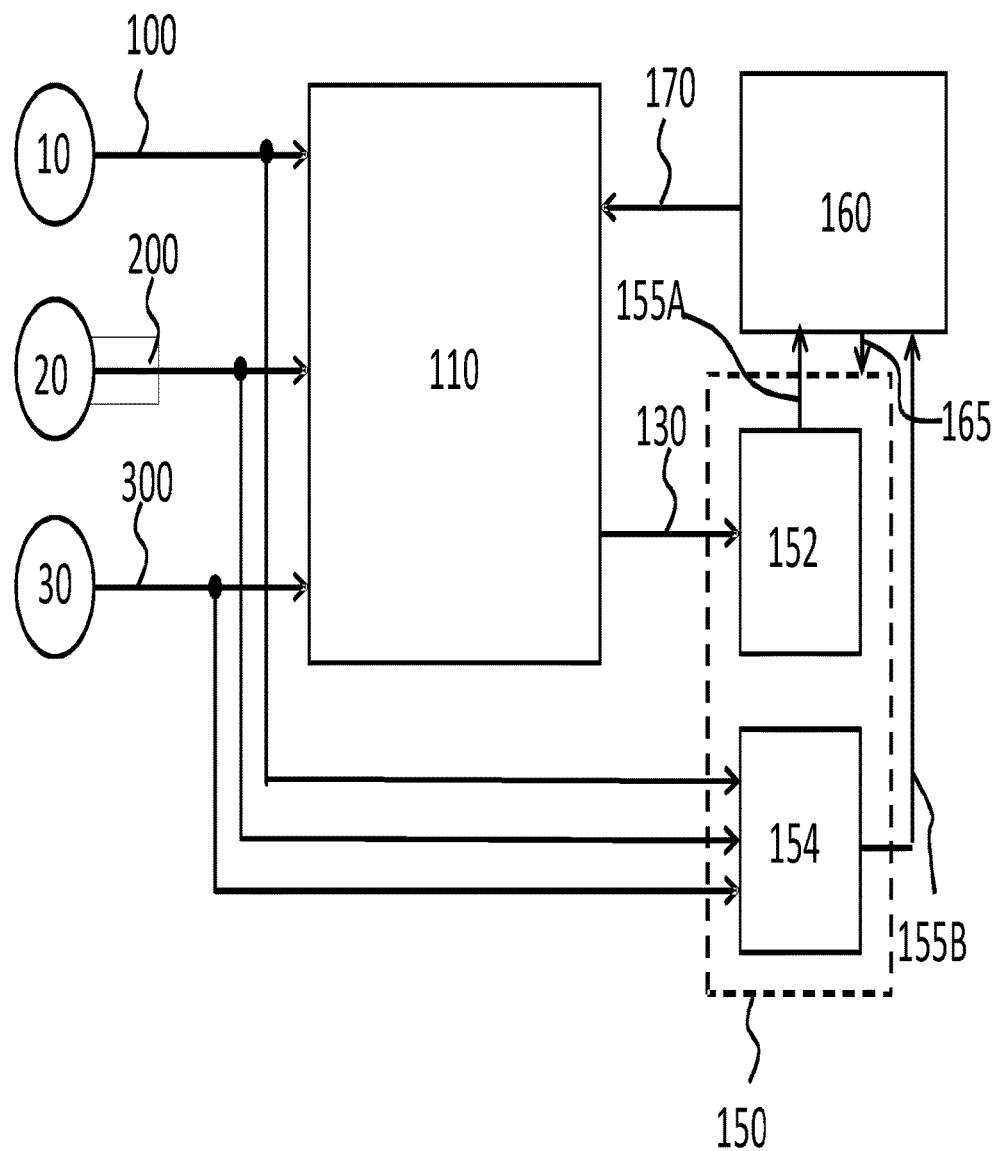
FIG. 2A is a simplified block diagram of a system for monitoring activities of daily living, ADLs, of a person within an environment according to an embodiment.

FIG. 2A shows an embodiment of a system according to the invention comprising a plurality of sensors 10, 20, 30 arranged to measure a property of at least one of: the person; and the environment in which the person is in.

Here, the first sensor 10 is a sensor that is adapted to detect a value of an ambient condition parameter of the environment, such as temperature or humidity for example. The second sensor 20 is a movement sensor 20 adapted to detect movement of the person that is monitored. The third sensor 30 is a power sensor 30 adapted to detect a value of the power consumption of an electrical appliance used by the person within the environment. The first 10, second 20 and third 30 sensors are adapted to output first 100, second 200 and third 300 sensor output signals, respectively, which are representative of the detected value(s).

The sensors 10,20,30 communicate their output signals 100,200,300 via wired or wireless connection. By way of example, the wireless connection may comprise a short-to-medium-range communication link. For the avoidance of doubt, short-to-medium-range communication link should be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), ISM Band, Near Field Communication (NFC), RFID, 6LoWPAN, UWB, Wireless HART, Wireless HD, Wireless USB, ZigBee. Examples of medium-range communication links include Wi-Fi, Z-Wave.

The system further comprises an ADL inference unit 110 adapted to receive the first 100 to third 300 sensor output signals, to infer an ADL of the person based on the received sensor output signals. The ADL inference unit 110 is further adapted to generate an inferred ADL output signal 130 representative of an inferred ADL of the person.

The system also comprises a monitor unit 150 adapted to receive the inferred ADL output signal 130 and the first 100 to third 300 sensor output signals. The monitor unit 150 is adapted to generate (and output) alert signal 155 indicating that the person may need direct assistance or indicating a potential deteriorating health condition of the person.

More specifically, the monitor unit 150 comprises first 152 and second 154 sub-units.

The inferred ADL output signal 130 is provided as an input to the first sub-unit 152 of the monitor unit 150, and the first sub-unit 152 of the monitor unit 150 generates an inferred alert signal 155A dependent on the inferred ADL output signal 130. In this way, the first sub-unit 152 of the monitor unit 150 uses information about the inferred ADLs to enable the creation of an alert signal 155A.

Conversely, the first 100 to third 300 sensor output signals are provided as inputs to the second sub-unit 154 of the monitor unit 150. In this way, second sub-unit 154 of the monitor unit 150 is provided with raw sensor data/signals directly (i.e. by-passing the ADL inference unit 110). The second sub-unit 154 of the monitor unit 150 is adapted to generate a second alert signal 155B directly dependent on the first 100 to third 300 sensor output signals. In this way, the second sub-unit 154 of the monitor unit 150 uses raw sensor data/signals to enable the creation of highly specific and/or accurate second alert signal 155B.

The system further comprises a user interface 160 for providing and receiving information to/from one or more users. Both the inferred alert signal 155A and the second alert signal 155B are provided to the user interface 160. Based on the received alert signals 155A and 155B, the user interface is adapted to communicate a signal or message to a user. In this way, the system may indicate that the person is in need of help. For example, the user interface 160 may be used to advise a medical practitioner, a caregiver, a family member or close relative to attend to the person. Alternatively, or in addition, the user interface 160 may be adapted to communicate a signal or message to the monitored person. For example, the user interface 160 may communicate a message advising the person to take a particular medication.

In this embodiment, the user interface 160 is adapted to receive user inputs for defining or modifying one or more alert conditions. Based on such user inputs, the user interface provides an alert condition signal 165 (representative of the one or more alert conditions) to the monitor unit 150, and the monitor unit 150 then generates the alert signals 155A and 155B further dependent on the one or more alert conditions.

Figure 2B:
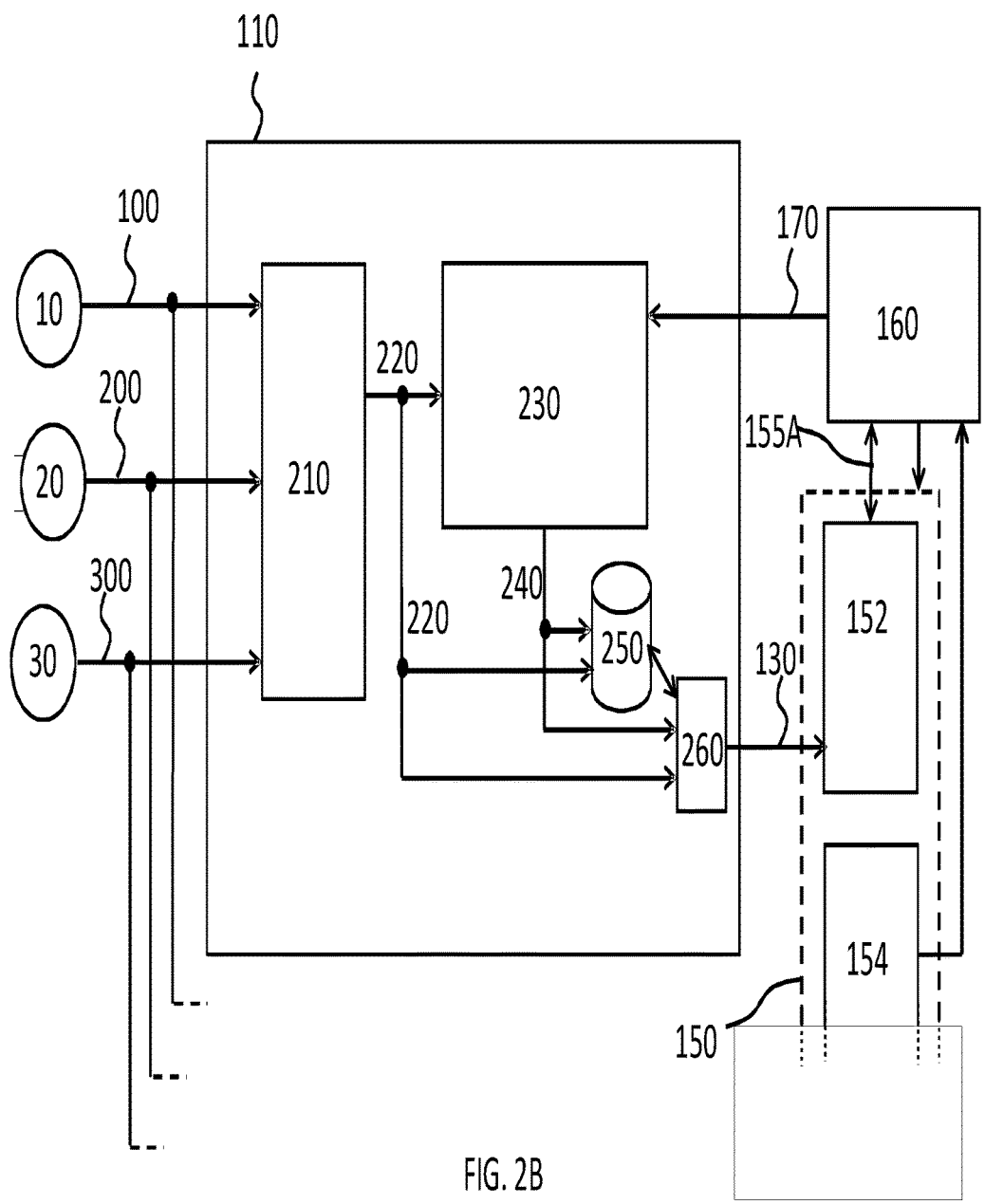
FIG. 2B is a simplified block diagram of an embodiment of the ADL inference unit in the system of FIG. 2A.

The user interface 160 is also adapted to receive user inputs for defining or modifying one or more ADL inference rules, instructions or conditions. Based on such user inputs, the user interface provides an inference signal 170 (representative of the one or more ADL inference rules, instructions or conditions) to the ADL inference unit 110, and the ADL inference unit 110 then generates the inferred ADL output signal(s) 130 further dependent on the one or more ADL inference rules, instructions or conditions provided by the user. FIG. 2B shows an embodiment of the ADL inference unit 110 in the system according to the invention. The ADL inference unit 110 is arranged to interpret the first 100 to third 300 sensor output signals and to generate an inferred ADL output signal 130 representative of one or more inferred ADLs of the person. Although not depicted, a receiving interface of the inference unit 110 may sample and timestamp the first 100 to third 300 sensor output signals sampled. By this it is meant that time information may be added to the sampled first 100 to third 300 sensor output signals.

The ADL inference unit 110 comprises a first inference subsystem 210 adapted to receive the first 100 to third 300 sensor output signals. Based on the first 100 to third 300 sensor output signals, the first inference subsystem 210 infers a primitive ADL event and generates a primitive ADL signal 220 representative of the inferred primitive ADL event.

The primitive ADL signal 220 is provided to a second inference subsystem 230. Based on the primitive ADL signal 220, the second inference subsystem 230 is adapted to infer the occurrence of one or more aggregate ADL events using a rule-based inference method. The second inference subsystem 230 then generates an aggregate ADL signal 240 representative of the inferred aggregate ADL event(s).

The ADL inference unit 110 further comprises a datastore 250 adapted to store information relating to ADLs that have been inferred by the first 210 and second 230 inference subsystems of the ADL inference unit 110. Both the primitive ADL signal 220 and the aggregate ADL signal 240 are provided to the datastore 250. The datastore 250 is thus adapted to implement an activity database in which information about inferred ADLs of the person is stored.

The ADL inference unit 110 also comprises an output unit 260 that is adapted to generate the inferred ADL output signal 130 dependent on at least one of: the primitive ADL signal 220; and the aggregate ADL signal 240. For this, the output unit 260 is adapted to receive the primitive ADL signal 220 and the aggregate ADL signal 240. In addition, the output unit 260 is adapted to communicate with the datastore 250 so as to receive information about inferred ADLs stored in the activity (which may have been inferred from earlier versions of the primitive ADL signal 220 and the aggregate ADL signal 240, for example).

It will be understood that the embodiment of FIG. 2B uses a concept of basing the inference of ADLs from sensor signals using a rule-based process. Further, only a part of the inference method may employ a rule-based formalism, so as to reduce overall computational complexity. Put another way, only a sub-part of the ADL inference may be cast in a rule-based formalism.

Primitive ADL events may be inferred directly from raw sensor output signals (i.e. outside the rule-based inference system/method). Primitive ADL events may then serve as an input to the rules that create aggregate ADL events. Aggregate ADL events may thus be formed based on a plurality of primitive ADL events and/or aggregate ADL events. Below is an example inference for Toilet usage. The system has sensors in the toilet and is adapted to infer when the person is on the toilet and how often he/she is visiting the toilet. The system has configuration information about the sensors, such as sensorID
    sensorType
    spaceID
    applianceID
    time
    key
    val
    The sensors used in this example Toilet ADL:
    PIR sensor in toilet
    sensorType=MotionSensor
    PIR sensor in bathroom, with toilet appliance
    sensorType=MotionSensor
    Pressure mat in front of toilet
    sensorType=PressureSensor
    Also used is a parameter that can be set by the system, or modified through the user interface:
    ToiletDurationThreshold
    Used in the generation of primitive events
    Default=0
    Param.Toilet_gap
    Threshold for aggregation of primitive events
    For example 600 sec In this example, Primitive and Aggregate Events hold the following fields/parameters
ID
TYPE
SPACE
WHEN
DUR
VAL Also, in this example the following three events are defined:
Primitive Event
ID: Toilet
TYPE: Present
Aggregate Event
ID: Toilet
TYPE: Used
Aggregate Event
ID: Toilet
TYPE: #Visits Event creation (for example in the first inference subsystem 210 of FIG. 2)

This creates Primitive Events. Below an example is expressed in pseudo code. Although 'if, then' statements are used, any programming language may be used and not necessarily to be casted and provided in a rule language. The inputs are the sensors signals 100, 200, 300.

```
atToilet= false;
toiletLeave= false;
for ev=1:nrEvents { // nrEvents: number of sensor events
  if DataEvent(ev).spaceID == "Toilet" { //DataEvent is an
  event in the input
signal from the sensors
    if atToilet == false {
    if DataEvent(ev).sensorType == "MotionSensor" &&
        DataEvent(ev).val == true {
      atToilet= true;
      toiletBegin= DataEvent(ev).time;
    }
    if Data.event(ev).sensorType == "PressureSensor" &&
        DataEvent(ev).val == true {
      atToilet= true;
      toiletBegin= DataEvent(ev).time;
    }
  }
  if atToilet == true {
    if DataEvent(ev).sensorType == "MotionSensor" &&
        DataEvent(ev).val == false {
      atToilet= false;
      toiletLeave= true;
      toiletEnd= DataEvent(ev).time;
    }
    if DataEvent(ev).sensorType == "PressureSensor" &&
        DataEvent(ev).val == false {
      atToilet= false;
      toiletLeave= true;
      toiletEnd= DataEvent(ev).time;
    }
  }
}
//
  if DataEvent(ev).spaceID) == "Bathroom" && DataEvent(ev).
    applianceID ==
"Toilet" {
    if atToilet == false {
    if DataEvent(ev).sensorType == "PressureSensor" &&
        DataEvent(ev).val == true {
    atToilet= true;
    toiletBegin= DataEvent(ev).time;
    }
  }
  if atToilet == true {
    if DataEvent(ev).sensorType == "PressureSensor" &&
        DataEvent(ev).val == false {
    atToilet= false;
    toiletLeave= true;
    toiletEnd= DataEvent(ev).time;
    }
  }
}
//
if toiletLeave == true {
toiletLeave= false;
tDur= time2Sec(toiletEnd) − time2Sec(toiletBegin);
if tDur > ToiletDurationThreshold {
//Create event
EventP[evCnt++]=
    o    ID: "Toilet"
    o    TYPE: "Present"
    o    SPACE: DataEvent(ev).spaceID
    o    WHEN: ToiletBegin
    o    DUR: tDur
    o    VAL: true
  }
}
}//for-ev
```

Aggregate rules (for example in the second inference subsystem 230 of Figure 2)

This operates code in a rule engine, hence the code is expressed in a rule language. One assumes that the engine includes support for functions like incrementing a counter, like the nrTlt in this example. A system like Drools is providing such support. In the example, the rules are kept simple and expressed in a pseudo language, to ease reading. In an embodiment, the rules are to be expressed according to the grammar of the used rules engine, such as, for example, the Drools system.

```
nrTlt= 0 // number of toilet visits
IF
[
Event .ID==Toilet
AND
Event .TYPE==Present
  //The rule engine will ensure all events are searched,
  //This condition statement ensures all (primitive) events of interest are
selected.
  //in this way an iteration over all these (primitive) events is induced.
]
```

```
THEN
[
    IF
    [
Event .WHEN AFTER TODAY
//"Event" indicates the selected event in the premise of the rule
AND
NOT EXIST(Event.ID==Toilet AND Event.TYPE==#Visits)
]
THEN
[
Create Event
    •    ID: Toilet
    •    TYPE: #Visits
    •    SPACE: Event.SPACE // Event.ID= Toilet && Event.TYPE==Prsent
    •    WHEN: ToiletBegin
    •    DUR: ToiletEnd − ToiletBegin
    •    VAL: nrTlt
// an aggregate event is added to data base 250
]
ELSE
    //in general, rule engines do not support an "ELSE" clause. In this case the IF
part (premise/condition/antecedent) has to be repeated, testing on the negation, and this
"ELSE" part becomes the "THEN" part of that rule (conclusion/consequent).
    ]
    nrTlt++;
    Update Event
    •    ID: Toilet
    •    TYPE: #Visits
        •    VAL: nrTlt
    tWHEN= EventP(ev).WHEN;
    tDUR= EventP(ev).DUR;
    tSPACE= EventP(ev).SPACE;
    //Rule part
    nrTlt++
    Aggregate= SELECT (Event.ID==Toilet AND Event.TYPE==Used) //
shorthand for all aggregates in database 250
    IF NOT EXIST(Aggregate)
    [
    Create Event
        ■    ID= "Toilet"
        ■    TYPE= "Used"
        ■    SPACE= tSPACE
        ■    WHEN= tWHEN
        ■    DUR= tDUR
        ■    VAL= 1
    ]
    ELSE
    [
    IF Event.WHEN < Aggregate.WHEN + Aggregate.DUR + Param.Toilet_gap
    [
    Aggregate.DUR= Event.WHEN + Event.DUR − Aggregate WHEN;
    Aggregate.VAL++
    //Update aggregate for longer duration of being on toilet
    ]
    ELSE
    [
    EventA[agCnt++]=
        ■    ID= "Toilet"
        ■    TYPE= "Used"
        ■    SPACE= tSPACE
        ■    WHEN= tWHEN
        ■    DUR= tDUR
        ■    VAL= 1
    // primitive event is later from aggregate, start new aggregate
    ]
    ]
    ]
]
```

From the example, it will be seen that the ID plus TYPE fields together allow the primitive and aggregate events to be distinguished (in the rules).

In the embodiment of FIG. 2B, the second inference subsystem 230 is adapted to receive an inference signal 170 that is representative of the one or more ADL inference rules, instructions or conditions defined by a user. Here, the inference signal 170 is provided via a user interface 160. The second inference subsystem 230 then infers the occurrence of one or more aggregate ADL events using a rule-based inference method further dependent on the ADL inference rules, instructions or conditions defined by a user.

The depicted embodiment thus enables a user of the system (such as the care giver or a medical practitioner, for example) to create, define, modify, alter rules and constraints for second inference subsystem 230. This can provide the flexibility to the many different contexts in which the system may operate.

Further, the order in which the rules are provided to the system can be arbitrary. This is because rules adhere to a so-called declarative approach. In usual programming languages, the algorithms are coded in the so-called imperative form, wherein the order of execution of the statements is relevant. By casting in the rule paradigm, a user can add rules without being concerned about the order in which they have to appear or be executed. This allows a user to define rules as they come to mind without the need to take care of a consistent programming flow or line of reasoning.

Thus, on the one hand, it is made easy for users to enter their rules. On the other hand, the system can be kept simple. There is no need to cover all possible situations for all potential users with their particular circumstances. Moreover, when users enter their own rules, these rules can be shared with other users, so that the total system enriches and refines itself.

Figure 3:
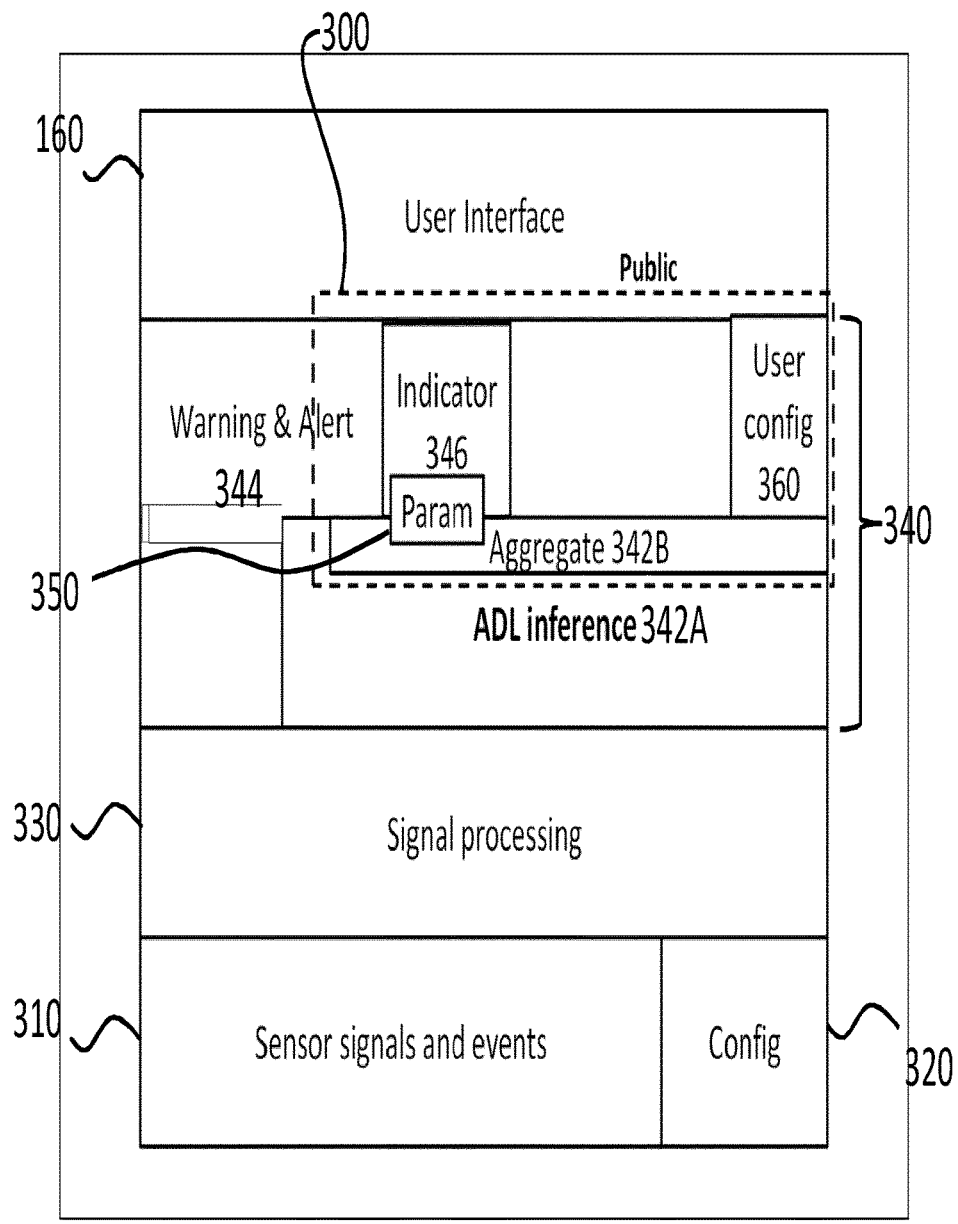
FIG. 3 is a layer diagram of the various layers of algorithms that together provide the data analytics to a system according to an embodiment.

Referring now to FIG. 3, there is depicted a layer diagram of the various layers of algorithms that together provide the data analytics to a system according to an embodiment. The algorithms are hosted on a (distributed) platform of which the encircled part 300, labelled "Public", is accessible to users of the system (using the user interface 160 for example).

At the lowest (i.e. bottom) layer, there is the system 310 of sensors (e.g. features 10,20,30 in FIG. 1) that issue signals, a continuous stream of data, and events, an irregular sequence of data. The data can be binary, e.g. open/close, or multi-valued, e.g. $CO_2$ concentration. They can also be multi-dimensional as in the case of accelerometers. This layer ensures reliable transmission and storage of the data, including their time-stamping and synchronization. Missed or unreliable sensor data, in so far identified, are repaired when possible and otherwise indicated as such.

Also in the lowest (i.e. bottom) layer, the sensor configuration information 320 is also maintained. The configuration information 320 is instantiated upon installation of the system and maps the physical location of each sensor to its functional meaning.

Physical location includes aspects like the room, the furniture, and/or the appliance the sensors are attached to.

Functional meaning is the type of information the sensor provides to the algorithms, for example "drawer holding cutlery".

A single sensor may map to multiple functional meanings. For example, a sensor may be used to infer activity in Eating, Drinking or in Bathing. The floorplan or layout of the environment (e.g. building, ward, or house) is also stored in the configuration information 320. The floorplan/layout informs about matters like which rooms are adjacent (by doors), floor level, entrance door (can be front or back door, depending on user's habits) and other outdoors, and which functional rooms are physically collocated (for example, kitchen and dining room are a same physical space).

Directly above the lowest (i.e. bottom) layer, there are two layers of data processing: signal processing 330 and an (ADL inference) analytics layer 340. In the signal processing layer 330, data is cleaned, de-noised, quantized, and processed to extract features and to aggregate them into events. Preferably the data is processed to yield feature values that provide a more discriminative view on the data than the original raw data. Such processing will boost the classification and inference that is executed in the (ADL inference) analytics layer 340.

In the (ADL inference) analytics layer 340, there are at least three types of functions. The first concerns the inference of ADL events 342, the second the detection of anomalies 344 and risky situations that lead to Warnings & Alerts, and the third provides an Indicator function 346.

The ADL Inference block 340 turns the sensor events into ADL events. In one embodiment this function is largely based on simple decision-taking rules, but in other embodiments classification-based designs can be applied as they are known from the art of machine learning. Although the rules may appear simple from conceptual point of view, best implementation can still be through an imperative coding paradigm. This also warrants compatibility, and hence eases incorporation, of the classification-based designs. Still, for the interaction with user-provided rules, the inferred ADL events are output into a rule based paradigm.

By this separation, accurate inference is enabled on the one hand, while, on the other hand, one can benefit from the flexibility that the rule paradigm offers. In particular, by implementing in the public part 300, customization and personalization of the (ADL monitoring) application is enabled.

More precisely, the ADL Inference consists of two stages (layers) 342A and 342B. In the first stage 342A, the (raw or pre-processed) sensor data is analysed and converted into so-called primitive ADL events. In the second layer 342B, these primitive ADL events are aggregated to meaningful ADL events, as an end-user is interested in the elder's activities and behaviours.

For example, when the person is busy in the kitchen preparing a meal, many primitive "EatingDrinking" events may be raised. These primitives are aggregated into a single ADL event, holding a certain duration. The first part 342A is implemented in a lower-layer of the ADL Inference block 340, which is a proprietary environment, whilst the aggregation part 342B is implemented in a higher layer of the ADL Inference block 340, which is in the public (rule-based) environment 300.

It is noted that ADL Inference block 340 may also, or only, output aggregate ADL events. For example, when a classifier is used that is trained to classify at once a sequence of ADL events epochs over a day, the output as entered into the public rule system is necessarily of aggregate type of events.

The output of the first part 342A, the primitive ADL events, are stored in the rule-based environment (as facts), so they are potentially available to other (analytics) rules sets. Preferably, an ADL event (fact) holds the following fields 1. ID—The ADL that is inferred.
2. TYPE—The type of the event, for the given ID (ADL).
3. SPACE—The physical location to which the event associates.
4. WHEN—The start moment in dd/mm/yyyy—hh:mm that the ADL (event) is detected.
5. DURATION—The duration in hh:mm the ADL is observed. If the event is instantaneous, the DUR is set to zero.
6. VALUE—The value of the event.

Warning & Alerts are derived from either the processed sensor data, from the primitive ADL events, or from the aggregate ADL events. Thus, the Warning and Alerts layer extends across the whole of the ADL Inference block 340 as depicted in FIG. 3.

An example algorithm to detect aberrations from the (processed) sensor data is as follows. In a first phase, the algorithm collects the sensor data and estimates the distribution in which they occur over the day. This can also be done offline, before installation, in which case the distributions represent the pattern is encountered in general, or encountered for the typical population to which the current elder belongs. The offline distribution can also be used to initiate the system. The obtained distributions serve as a reference. In the second phase, upon operation, the sensor data of the current day is collected and that pattern is tested against the reference pattern (distribution). Note that the reference distribution can be updated over time, by using the data of the recent days (and fading out those of earliest days, or from the initiation). A pattern can be considered as outlying if its probability (in terms of the reference distribution) is below a pre-defined (chosen) threshold.

The Indicator function is a signalling means that is used for presentation in the user interface, for example a dashboard displaying the different ADLs as they have been performed by the person. An example indicator would be that the ADL events are tested against their duration and rate of occurrence. If they pass a given threshold, the ADL is presented in another way (other color, other size) in the UI. The thresholds are set in the block labelled "Param" 350. The Indicator is fully implemented in the (public) rule system 300.

The block "Param" holds configurable parameters. The parameters are used by the rules in the rule system. The thresholds, as used by the Indicator function 346, constitute one set of parameters. Another set is formed by the parameters that are used in the aggregation part 342B. By changing the parameters, a user can modify the aggregation and indication of the data in the user interface 160 views.

The user config block 360 is another exemplary block. It allows a user to compose their own views of the ADL events as well as to set indicators on them. For example, a "bladder" view could be defined as the conglomerate of the ADLs Bed, Drinking, and Toilet. Thresholds can also be set through the user config block 360.

The user interface 160 is the uppermost (i.e. top) layer, and uses techniques as are generally known in the art. It encompasses all views, including alert routes, to the appropriate stakeholders, as well as the controls to set parameters, such as the thresholds. It can read the data (facts) in the (public) rule system and can be called by the Warning & Alert function 344.

The user interface layer 160 also contains post-processing tasks, possibly modelled as a separate layer within the user interface layer 160. The post-processing tasks relate to computations that drive the presentation. For example, denoting an ADL as a Day or Night event is a function performed in this layer.

Figure 4:
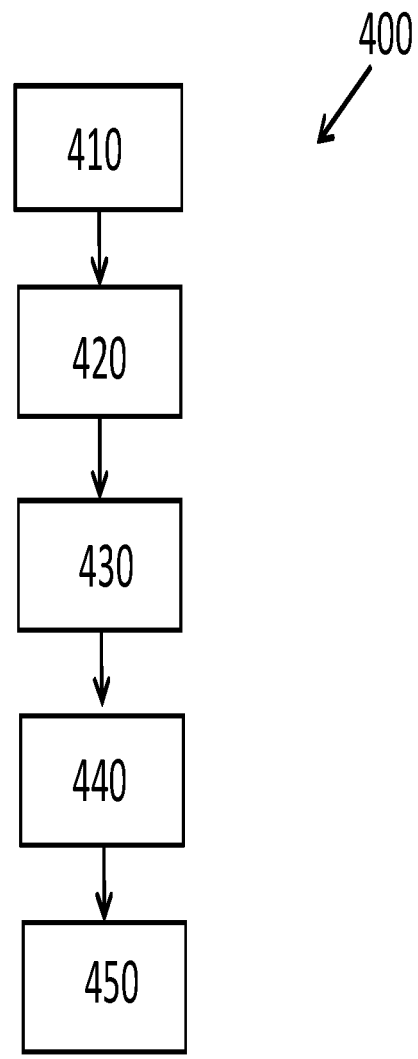
FIG. 4 is a flow diagram of a method for monitoring activities of daily living, ADLs, of a person within an environment according to an embodiment.

Referring now to FIG. 4, there is shown a flow diagram of a method 400 for monitoring ADLs, of a person within an environment according to an embodiment. The method 400 begins with the step 410 of detecting, with a sensor, a value of a property of at least one of: the person; and the environment. Next, in step 420, the sensor generates a sensor output signal representative of the detected value.

Based on the sensor output signal, an ADL of the person is inferred in step 430. Next, in step 440, an inferred ADL output signal is generated which is representative of the inferred ADL of the person.

Finally, in step 450, a monitor signal is generated dependent on at least one of: the sensor output signal; and the inferred ADL output signal.

The proposed method therefore generates a monitor signal from either of two types of information, or from a combination of both types of information. The first type of information relates to an ADL of the person that is inferred from a sensor output signal, whereas the second type of information relates to the sensor output signal itself. Thus, inferred ADLs may be used to generate a monitor signal dependent on the inferred ADLs. In this way, use of the inferred ADLs may enable the creation of simple warnings & alerts. The raw or processed (e.g. sampled, cleaned, time-stamped, etc) sensor data/signals may be used to generate a monitor signal dependent on the sensor data/signals directly. The sensor data/signals may therefore enable the creation of highly specific and/or accurate warnings and alerts.

Figure 5:
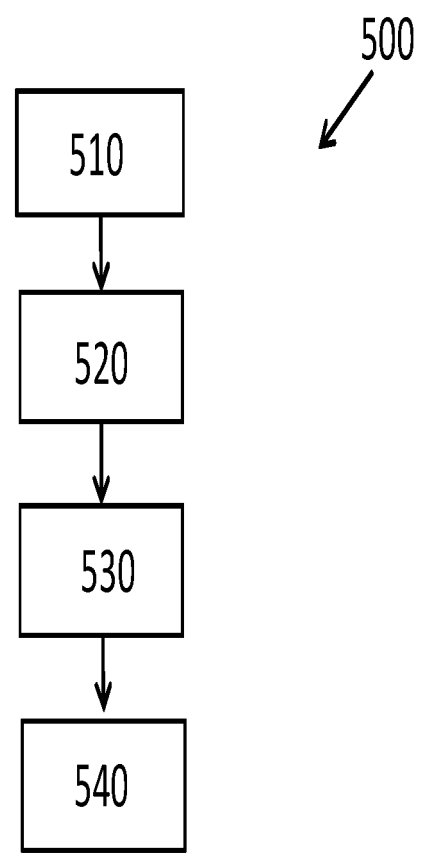
FIG. 5 is a flow diagram of a method for inferring an ADL of a person based on a sensor output signal according to an embodiment.

Referring now to FIG. 5, there is shown a flow diagram of a method 500 for inferring an ADL of a person based on a sensor output signal according to an embodiment.

The method begins with step 510 in which a primitive ADL event is inferred based on the sensor output signal. Next, in step 520, a primitive ADL signal representative of the inferred primitive ADL event is generated.

An aggregate ADL event is then inferred, in step 530, using the primitive ADL signal in accordance with a rule-based inference method.

Finally, in step 540, an aggregate ADL signal is generated which is representative of the inferred aggregate ADL event, Based on the generated signals (i.e. the primitive ADL signal and the aggregate ADL signal) an ADL of the person may be inferred. Thus, by way of example, the method 500 for inferring an ADL of a person may be implemented in step 430 of the previously described method 400 for monitoring ADLs of a person (depicted in FIG. 4). In particular, the step 430 of generating an inferred ADL output signal may be dependent on at least one of: the primitive ADL signal; and the aggregate ADL signal.

Of course, it will be understood that the described method 500 for inferring an ADL may be implemented in other method and/or systems.

Rule, Ontology and Other Logic-Based Systems

Support for conditions in arbitrary order and not requiring any program flow is provided by using a declarative, logic format. In general, as is widely known in the art, the language of logic programs is composed of so-called statements between entities. An entity can be a class (set) or an instantiation (element) of that class. The statements express membership of an element in a set and relations between sets (one is subset of another, etc). In this way the knowledge can be described, while the order of statements can be arbitrary.

Ontologies are known in the art. They provide a means to encode for machine interpretation the relationships between concepts and objects as they are known in the domain at hand. For example, an ontology can be used to express that a "room" "is part of" "house". In his example "house" and "room" are objects that are related to each other by "is part of". The ontology can continue with statements that express the furniture in each room, as well as what type of furniture there is. For example, "kitchen" "is a" "room"
"drawer_cutlery" "is a" "cupboard"
"refrigerator" "is part of" "kitchen"
"refrigerator" "is a" "cupboard"
"cutlery" "is part of" "drawer_cutlery"
etc In this way, a whole domain, in this example a house, can be described. For example, it can now be inferred that "kitchen" "is part of" "house". For this to happen, the semantics of the terms in the ontology need to be defined. This can be done in several ways. One form is to use so-called entailment rules that describe, in a complete manner, the inferences that statements can imply. For example an entailment rule defining "is a" is IF [A R B] AND [C "is a" A] THEN [C R B]

There can be more rules related to "is a". Here A, B, and C are objects and R is a relation. In the above example, R is "is part of" and A, B and C are "room", "house", and "kitchen", respectively. In evaluating the ontology, all statements are tested for the entailment rules defining the semantics of the ontology and the implied statements are added to the ontology. This process is repeated until closure is obtained (no further statements are added to the ontology).

As an example, consider a household where the cutlery is stored in a basket on a shelf in the kitchen. When, upon installation of the sensor system, the basket holding the cutlery is associated with "cutlery", it also becomes associated with "drawer_cutlery" and the intelligence that infers the ADLs can be programmed in terms of the "drawer_cutlery", where the ontology takes care that the provided installation information (cutlery sensor attached to basket) links the program to the sensor at the basket.

A professional installer can be instructed to link the sensor to the "drawer_cutlery" and the ontology layer can be bypassed. For arbitrary users, who add rules at the "public" layer in FIG. 3, such an ontology can further ease the way(s) the additional rules are added.

Here, we take advantage of the fact that the semantics of an ontology can be defined in terms of rules, the so-called entailment rules. Instead of having a separate function that evaluates and processes the semantics, so as to connect the terminology in the user-provided rules with the rules and (user) interface intelligence part of the system, see FIG. 3, the rule base is expanded with the entailment rules defining the semantics of the ontology. The rule engine will evaluate the combined set of system-rules (rules defined by the owner of the system), user-rules (rules added by the user), and entailment-rules (rules defining the semantics of the ontology). In order to minimize computational complexity, the implementation of the rule engine can take advantage of these different kind of rules, so that the evaluation of the rules can be performed more efficiently.

Note that a subset relation can also be viewed as a rule ("set A is a subset of set B" is the same as "if A then B"). In the user interface 160, the user can enter information (e.g. constraints) in the form of rules. A rule is composed of a condition and a (set of) conclusion(s). The condition can be composed of several conditions, using logical operators (AND, OR, NOT). Each primitive condition and conclusion is a statement.

The set of rules form a network, where a conclusion from one rule constitutes (part of) the condition of another.

Instead of logical operators, it is also possible to use probabilities, so that the network becomes a probabilistic network, such as a Bayesian Network. In such a case, a decision is needed at the nodes that interface to the user interface, i.e. a decision whether/what message (conclusion) to present in the user interface.

By using a declarative language, the rules can be entered in any order. The rule engine pulls them together. Also, given the form of statements (rules), the user interface 160 can be kept simple: there are entrance fields for conditions, using the logical connectors, and fields for conclusions. Examples of particular fields are the ADLs, the time of day, temporal relationships, and the parameters (thresholds). A known way in the art to represent temporal relationships is Allen's temporal logic.

In order to simplify the user interface 160 further, the rule base can be divided in rules of different nature. There are three main categories, called Knowledge base (KB), Configuration, and Observations.

The KB holds general statements (rules) and can be delivered to a user to enrich the system, possibly in a module per module way. Example rules for a KB are rules that set up temporal relationships, such as Allen's algebra. These rules capture the notion of "preceded" and "recently", so the user can use them when composing particular (use-case) rules. Another example includes rules that describe general truths of a house, for example defining the notion of upstairs and ground level, such that rooms can be declared to be upstairs. The rule set (module) can also define that rooms upstairs can only be accessed by walking the stairs. It can define special functions to rooms, like batch room, living room, bed room, kitchen, and toilet. Etc.

Configuration holds rules that are to be entered once. They are typically entered upon installation of the (sensor) system. For example they declare the number of rooms in the user's house, the location of their doors (what room connects to what other room), whether they are upstairs, etc.

Finally, Observations is a dynamic part. It holds rules that connect sensor measurements to the ADLs. The majority of the rules appear as facts (only the conclusion part of a rule/the conditional part always being TRUE) and constitute the primitive ADLs, for example. This rule set is dynamic, since it captures the sensor readings, which obviously change over time.

During operation, a reasoner (e.g. a processor or rule engine) can pre-process the rules in the KB. Also, the rules in Configuration can be pre-processed in so far that they do not depend on unresolved rules, such as the rules depending on the statements in the Observation part. The Observation part is regularly refreshed. Instead of processing the rules in the observation parts through dynamically updating statements in the full rule base, the inference engine can be modified to implement these parts directly. Once the inference engine has built the full network of rules, the Observation rules link to the "entrance" nodes of the network and hence their effect can be automated.

Example Rules for ADL Inference

Upon installation, the sensors 10,20,30 are mounted in the monitoring environment (e.g. the monitored person's home). The sensors 10,20,30 have a physical ID and are associated with physical location or physical appliances (furniture) in the environment. In the first layer (FIG. 3), these identifiers are converted/extended with functional IDs. applianceID is the identifier of the functional object that a sensor is responding to, in case the person is interacting with the object. It may happen that a same physical sensor is used to provide data for different applianceIDs. For example, a sensor may be used to infer activity in Eating, Drinking or in Bathing. This is unknown at this analytics layer. applianceID can refer to a room, for example "living room" or "kitchen". It can also refer to a piece of furniture to which the sensor is mounted or which the sensor is observing. Examples include "refrigerator", "entrance door", and "cupboard drawer holding cutlery".

Sensor events are indexed with a counter "k". The index "k" indicates the currently observed event instant. "k−1" and "k+1" indicate the preceding and the next subsequent event from this sensor. Note that "k" refers to different times, since it is conditioned on the sensor identified by applianceID.

The field Time indicates the time at event "k" of sensor "applianceID". Time holds precision at minute granularity, i.e. time holds year, month, day, hour and minute.

Figure 6:
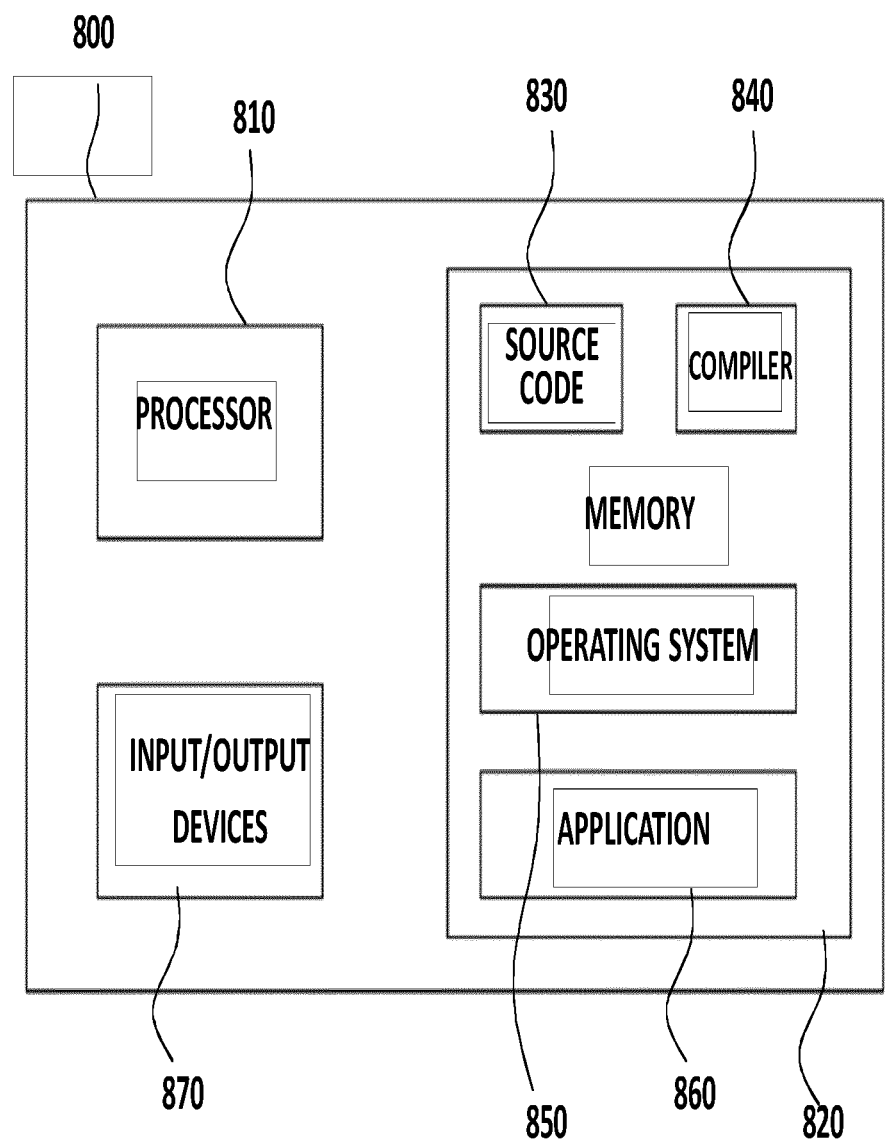
FIG. 6 is a simplified block diagram of a computer within which one or more parts of an embodiment may be employed.

FIG. 6 illustrates an example of a computer 800 within which one or more parts of an embodiment may be employed. Various operations discussed above may utilize the capabilities of the computer 800. For example, one or more parts of an AV or an automated delivery system may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A system for monitoring activities of daily living, ADLs, of a person within an environment, the system comprising:
    an ADL inference unit adapted to receive a sensor output signal representative of a detected value of a property of at least one of: the person; and the environment, and to generate an inferred ADL output signal representative of an inferred ADL of the person; and
    a monitor unit adapted to generate a monitor signal dependent on at least one of: the received sensor output signal; and the inferred ADL output signal,
    wherein the ADL inference unit comprises:
    a first inference subsystem adapted to receive the sensor output signal, to infer a primitive ADL event based on the received sensor output signal, the primitive ADL event being an event directly inferable from at least one sensor output signal, and to generate a primitive ADL signal representative of the inferred primitive ADL event; and
    a second inference subsystem adapted to receive the primitive ADL signal, to infer an aggregate ADL event from the received primitive ADL signal, the aggregate ADL event being an event based on at least one primitive ADL event, and to generate an aggregate ADL signal representative of the inferred aggregate ADL event, and wherein ADL inference unit is adapted to generate the inferred ADL output signal based on the primitive ADL signal and the aggregate ADL signal.

2. The system according to claim 1, wherein the second inference subsystem is adapted to infer the aggregate ADL event from the received primitive ADL signal using a rule-based inference method.

3. The system according to claim 2, further comprising a rule input interface adapted to receive an input for defining or modifying one or more rules of the rule-based inference method.

4. The system according to claim 1, further comprising a user input interface adapted to receive a user input for defining or modifying one or more alert conditions, and wherein the monitor unit is adapted to generate the monitor signal further dependent on the one or more alert conditions.

5. The system according to claim 1, wherein the monitor unit is adapted to generate the monitor signal based on a comparison of the received sensor output signal with a predetermined threshold.

6. The system according to claim 1, wherein the inferred ADL of the person is taken from a group comprising one or more of: eating, cooking, medicating, sleeping, toileting, bathing, or washing.

7. The system according to claim 1, wherein the ADL inference unit is further adapted to store the inferred ADL of the person in an activity database.

8. The system according to claim 7, wherein the monitor unit is further adapted to detect an irregularity in the activity database, and wherein the monitor unit is further arranged to generate the monitor signal as an alert signal in response to the detected irregularity.

9. The system according to claim 8, wherein the monitor unit is further adapted to determine a frequency of the ADL in the activity database, the detected irregularity being dependent on a change in the frequency.

10. The system according to claim 1, further comprising a sensor adapted to detect a value of a property of at least one of the person and the environment, and to generate the sensor output signal representative of the detected value.

11. The system according to claim 1, wherein the system is adapted to provide the generated monitor signal to at least one of the person, a medical practitioner, or a caregiver.

12. A method for monitoring activities of daily living, ADLs, of a person within an environment, the method comprising:
    inferring an ADL of the person based on a sensor output signal representative of a detected value of a property of at least one of: the person; and the environment;
    generating an inferred ADL output signal representative of the inferred ADL of the person; and
    generating a monitor signal dependent on at least one of: the sensor output signal; and the inferred ADL output signal,
    wherein the step of inferring an ADL comprises:
    inferring a primitive ADL event based on the sensor output signal, the primitive ADL event being an event directly inferable from at least one sensor output signal;
    generating a primitive ADL signal representative of the inferred primitive ADL event;
    inferring an aggregate ADL event from the primitive ADL signal, the aggregate ADL event being an event based on at least one primitive ADL event; and
    generating an aggregate ADL signal representative of the inferred aggregate ADL event, and wherein the step of generating an inferred ADL output signal ADL is based on the primitive ADL signal and the aggregate ADL signal.

13. The method of claim 12, further comprising storing the inferred ADL of the person in an activity database, wherein generating a monitor signal comprises detecting an irregularity in the activity database and generating an alert signal in response to the detected irregularity.

* * * * *